United States Patent [19]

Nagano et al.

[11] 4,437,877

[45] Mar. 20, 1984

[54] 2-(2-FLUORO-4-HALO-5-SUBSTITUTED PHENYL) HYDANTOINS AND USE

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Osaka, all of Japan

[73] Assignee: Sumitomo Chemical Company, Limited, Osaka, Japan

[21] Appl. No.: 387,275

[22] Filed: Jun. 10, 1982

[30] Foreign Application Priority Data

Jun. 16, 1981 [JP] Japan ................................ 56-93315
Dec. 4, 1981 [JP] Japan ................................ 56-196035
Dec. 4, 1981 [JP] Japan ................................ 56-19036

[51] Int. Cl.³ .................. A01N 43/90; C07D 471/04; C07D 513/04
[52] U.S. Cl. ........................................ 71/90; 71/91; 71/90; 544/48; 544/58.2; 544/58.4; 546/121; 546/226
[58] Field of Search .............. 544/48; 546/121; 71/90, 71/91, 92

[56] References Cited

U.S. PATENT DOCUMENTS 3,958,976 5/1976 Goddard .................................. 71/92
4,179,276 12/1979 Cheng ..................................... 71/91

FOREIGN PATENT DOCUMENTS 1503244 3/1978 United Kingdom .

Primary Examiner—Richard Raymond
Attorney, Agent, or Firm—Birch, Stewart, Kolasch & Birch

[57] ABSTRACT

A herbicidal composition which comprises as an active ingredient a compound of the formula:

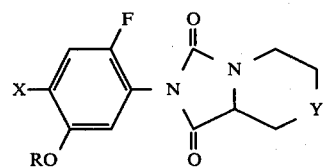

wherein X is a chlorine atom or a bromine atom, Y is —CH$_2$—, —S— or —SO$_2$— and R is a C$_1$-C$_4$ alkyl group, an allyl group or a propargyl group, and an inert carrier.

18 Claims, No Drawings

2-(2-FLUORO-4-HALO-5-SUBSTITUTED PHENYL) HYDANTOINS AND USE

The present invention relates to 2-(2-fluoro-4-halo-5-substituted phenyl)hydantoins (hereinafter referred to as "hydantoin(s)"), and their production and use.

The said hydantoins are representable by the formula:

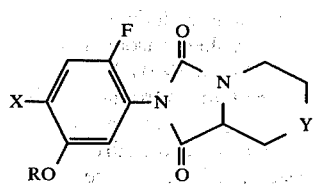

wherein X is a chlorine atom or a bromine atom, Y is —$CH_2$—, —S— or —$SO_2$— and R is a $C_1$-$C_4$ alkyl group, an allyl group or a propargyl group.

It is known that certain kinds of N-phenylhydantoins are effective as herbicides. For instance, the herbicidal use of 2-(4-chlorophenyl)-5,6,7,8-tetrahydroimidazo[1,5-a]pyridine-1,3(2H,8aH)-dione, 2-(4-chloro-2-fluorophenyl)-5,6,7,8-tetrahydroimidazo[1,5-a]pyridine-1,3(2H,8aH)-dione, 1,2-(4-chloro-2-fluorophenyl)-5,6,7,8-tetrahydro-1H-imidazo[5,1-c][1,4]thiadine-1,3(2H)-dione, 2-(4-chloro-2-fluorophenyl)-5,6,7,8-tetrahydro-1H-imidazo-[5,1-c][1,4]thiadine-1,3(2H)-dione-7,7-dioxide, etc. is disclosed in British Pat. No. 1,503,244, U.S. Pat. Nos. 3,958,976, 4,179,276, etc. However, their herbicidal effect is still not necessarily satisfactory.

It has now been found that the hydantoins (I) show a strong herbicidal activity against a wide variety of weeds including Gramineae weeds, Cyperaceae weeds and broad-leaved weeds at small doses and do not produce any material phytotoxicity on various agricultural crops (i.e. corn, soybean, cotton, rice plant, wheat). Examples of Gramineae weeds against which the hydantoins (I) show a herbicidal activity are barnyardgrass (*Echinochloa crus-galli*), green foxtail (*Setaria viridis*), large crabgrass (*Digitaria sanguinalis*), Johnsongrass (*Sorghum halepense*), wild oat (*Avena fatua*), water foxtail (*Alopecurus geniculatus*), goosegrass (*Eleusine indica*), annual bluegrass (*Poa annua*), bermudagrass (*Cynodon dactylon*), quackgrass (*Agropyron repens*), etc. Examples of broad-leaved weeds are tall morningglory (*Ipomoea purpurea*), velvetleaf (*Abutilon theophrasti*), sicklepod (*Cassia obtusifolia*), wild sunflower (*Helianthus annus*), cocklebur (*Xanthium pennsylvanicum*), wild mustard (*Brassica kaber*), common purslane (*Portulaca oleracea*), jimsonweed (*Datura stramonium*), hemp sesbania (*Sesbania exaltata*), sun spurge (*Euphorbia helioscopia*), black nightshade (*Solanum nigrum*), prickly sida (*Sida spinosa*), common ragweed (*Ambrosia artemisifolia*), smartweed sp. (Polygonum sp.), redroot pigweed (*amaranthus retroflexus*), bedstraw (*Galium aparine*), pineappleweed (Matricaria spp.), birdseye speedwell (*Veronica persica*), wild buckwheat (*Polygonum convolvulus*), beggarticks (Bidens spp.), common lambsquarters (*Chenopodium album*), bindweed (*Calystegia japonica*), monochoria (*Monochoria vaginalis*), Dopatrium junceum, waterwort (*Elatine triandra*), false pimpernel (*Lindernia procumbens*), toothcup (*Rotala indica*), arrowhead (*Sagittaria pygmaea*), etc. Examples of Cyperaceae weeds are nutsedge sp. (Cyperus sp.), *Cyperus rotundus, Ceperus esculentus,* hardstem bulrush (*Scirpus juncoides*), nutsedge (*Cyperus serotinus*), water chestnut (*Eleocharis kuroguwai*), slender spikerush (*Eleocharis acicularis*), etc. Accordingly, the hydantoins (I) can be used as herbicides applicable to paddy fields as well as agricultural plowed fields. They are also useful as herbicides to be employed for use in an orchard, tea garden, mulberry field, rubber plantation, forest, lawn, pasture, nonagricultural field, etc.

The hydantoins (I) can be produced by various procedures, among which typical examples are shown below:

PROCEDURE A

The hydantoin (I) is obtainable by reacting a phenyl isocyanate of the formula:

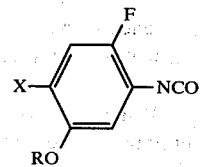

wherein X and R are each as defined above with an azine of the formula:

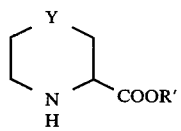

wherein R' is an alkali metal atom or an alkyl group and Y is as defined above in an inert solvent (e.g. water, toluene, hexane, benzene) at a temperature of from room temperature (ca. 20° C.) to the boiling temperature of the solvent to give an urea of the formula:

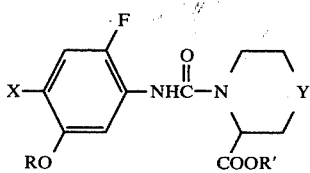

wherein X, Y, R and R' are each each as defined above, followed by treatment of the latter with a mineral acid such as hydrochloric acid or an alkali metal alkoxide such as sodium methoxide for ring closure.

PROCEDURE B

The hydantoin (I) is obtainable by reacting a hydroxyphenylhydantoin of the formula:

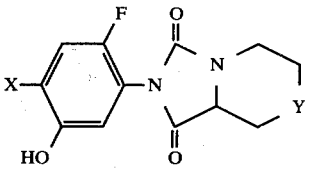

wherein X and Y are each as defined above with a halide of the formula:

R-Z (VI)

wherein Z is a chlorine atom, a bromine atom or an iodine atom and R is as defined above in the presence of a base (e.g. potassium carbonate, sodium hydroxide, sodium hydride, sodium alkoxide) in an inert solvent (e.g. dimethylformamide, dimethylsulfoxide, acetonitrile, methylethylketone, ethylene glycol monomethyl ether) at a temperature of 0° to 200° C. The molar ratio of the halide (V) and the base is preferred to be from 1.0 to 2.0.

PROCEDURE C

The hydantoin (I: Y=—SO₂—) is obtainable by oxidizing the corresponding hydantoin (I: Y=—S—) with a peracid (e.g. peracetic acid, perbenzoic acid, m-chloroperbenzoic acid) in the presence of an inert solvent (e.g. methylene chloride, chloroform) at a temperature of —30° to 30° C.

The thus produced hydantoin (I) may be, when desired, purified by a per se conventional procedure such as recrystallization or column chromatography.

The production of the starting materials are summarized in the following scheme:

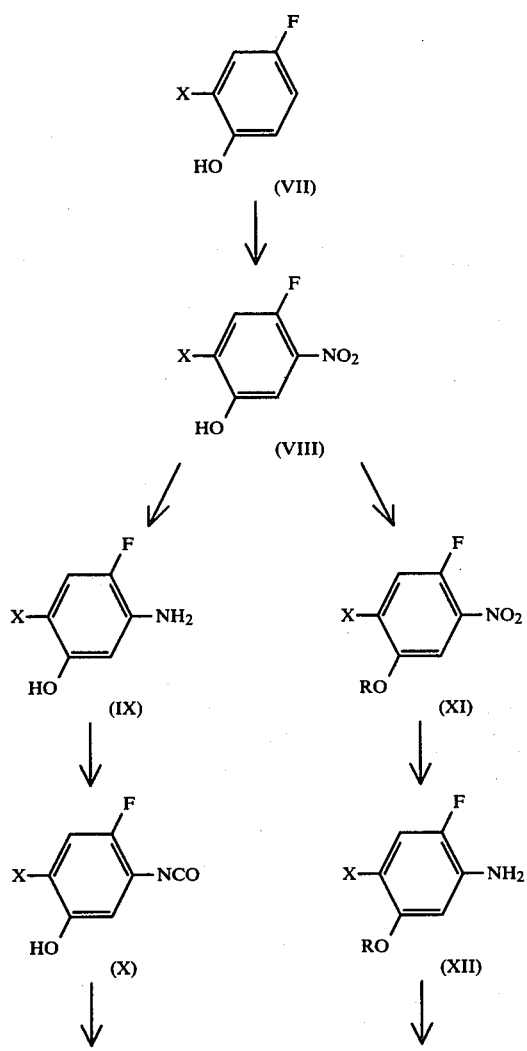

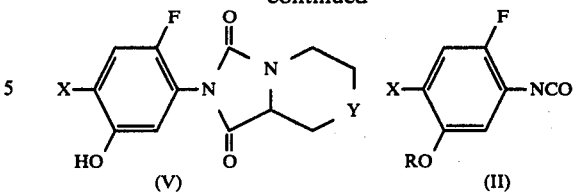

wherein X, Y and R are each as defined above.

Specifically, the hydroxyphenyl isocyanate (X) may be produced from the phenol (VII) by nitrating the same, subjecting the resultant nitrophenol (VIII) to reduction and reacting the resulting aminophenol (IX) with phosgene. The thus produced hydroxyphenyl isocyanate (X) is then reacted with the azine (III) to give the hydroxyphenylhydantoin (V). Also, the phenyl isocyanate (II) may be produced from the nitrophenol (VIII) by subjecting the latter to alkylation, alkenylation or alkynylation, reducing the resultant nitrobenzene (XI) and reacting the resulting aminobenzene (XII) with phosgene.

Explaining the above conversions more in detail, the nitration of the phenol (VII) into the nitrophenol (VIII) may be accomplished by application of a per se conventional nitration procedure to the former. Usually, however, the indirect nitration which consists of the following three steps is favorable in achievement of the selective nitration at the desired position:

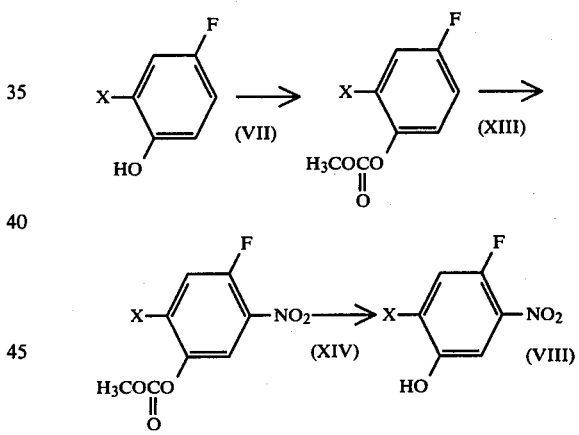

wherein X is as defined above. Thus, the phenol (VII) (Finger et al.: J.Am.Chem.Soc., 81, 94 (1959)) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water at a temperature of 0° to 10° C. The thus prepared carbonic ester (XIII) is nitrated with a mixture of conc. sulfuric acid and conc. nitric acid at room temperature. Then, the nitrobenzene (XIV) thus obtained is hydrolyzed with an aqueous solution such as an aqueous sodium hydroxide solution at a temperature of 40° to 80° C. to give the nitrophenol (VIII).

Reduction of the nitrophenol (VIII) into the aminophenol (IX) may be carried out by a per se conventional procedure for reduction of a nitro group on an aromatic ring to an amino group. Examples of such a procedure are reduction with sodium sulfide or iron powder, catalytic reduction, etc. Preferred are reduction with gaseous hydrogen in the presence of platinum dioxide as a catalyst in an amount of 1/10 to 1/100 mol to 1 mol of the nitrophenol (VIII) at room temperature under atmospheric pressure, and reduction of the nitrophenol (VIII) with iron powder (e.g. reductive iron, electrolytic iron) in an amount of 2.0 to 5.0 mol to 1 mol of the nitrophenol (VIII) in acetic acid at a temperature of 80° to 120° C., etc.

The reaction of the aminophenol (IX) with phosgene in an inert solvent (e.g. anhydrous ethyl acetate) gives the hydroxyphenyl isocyanate (X).

The hydroxyphenyl isocyanate (X) is reacted with the azine (III) at room temperature in an inert solvent (e.g. benzene, toluene, xylene), if necessary, by treatment with a mineral acid to give the hydroxyphenylhydantoin (V).

Alternatively, the alkylation, alkenylation or alkynylation for conversion of the nitrophenol (VIII) to nitrobenzene (XI) may be carried out by treatment of the former with an alkali metal carbonate (e.g. potassiumm carbonate), an alkali metal hydride (e.g. sodium hydride) or an alkali metal alkoxide (e.g. sodium methoxide) and reacting the resultant alkali metal salt with the halide (VI) in a polar solvent (e.g. water, dimethylformamide, acetonitrile, acetone, dimethylsulfoxide), usually at a temperature of 10° to 200° C., preferably of 30° to 100° C. The use of a phase transfer catalyst such as tetrabutylammonium bromide is favorable for smooth accomplishment of the reaction.

Reduction of the nitrobenzene (XI) to the aminobenzene (XII) may be achieved in various procedures. When, for instance, R in the compound (XI) is $C_1$-$C_4$ alkyl, there may be adopted a per se conventional reduction procedure for converting a nitro group into an amino group wherein a reducing agent such as sodium sulfide or iron powder or catalytic reduction is employed. One of typical procedures comprises introduction of a 3 molar amount of hydrogen into a reaction system comprising one molar amount of the compound (XI) and a 1/10 to 1/100 molar amount of platinum dioxide at room temperature under atmospheric pressure. Another typical procedure comprises admixing an acetic acid solution containing one molar amount of the compound (XI) with a 5% acetic acid solution containing a 2.5 to 5.0 molar amount of iron powder such as reductive iron or electrolytic iron and effecting the reaction at a temperature of 80° to 100° C. When R in the compound (XI) is propargyl or allyl, there may be adopted reduction with iron powder. For instance, an acetic acid solution containing one molar amount of the compound (XI) may be admixed with a 5% acetic acid solution containing 2.5 to 5.0 molar amount of iron powder such as reductive iron or electrolytic iron at a temperature of 80° to 120° C., preferably of 90° to 110° C., for a period of 0.5 to 5 hours.

The aminobenzene (XII) is converted into the phenyl isocyanate (II) by reacting the former with phosgene in an inert solvent (e.g. toluene, benzene, ethyl acetate, tetrahydrofuran, 1,4-dioxane).

Practical and presently preferred embodiments of the production of the objective hydantoins (I) as well as the intermediary compounds are illustratively shown below:

EXAMPLE 1

A solution of 4-chloro-2-fluoro-5-isopropoxyphenyl isocyanate (2.3 g) in chlorobenzene (10 ml) was added to a 2% aqueous solution of sodium hydroxide (25 ml) containing pipecolic acid (1.3 g), and the mixture was stirred at room temperature (ca. 20° C.) for 3 hours. After allowed to stand overnight, the precipitated crystals were collected by filtration and washed with ether. The crystals were combined with water (20 ml) and adjusted to pH 2 or less with hydrochloric acid, followed by reflux for 3 hours. After allowed to cool, the mixture was extracted with ether, dried and concentrated. The residue was purified by silica gel chromatography to give 0.6 g of 2-(4-chloro-2-fluoro-5-isopropoxyphenyl)-5,6,7,8-tetrahydroimidazo[1,5-a]pyridine-1,3(2H,8aH)-dione (Compound No. 7). M.P. 60.5°-64.5° C.

NMR (CDCl$_3$), δppm: 1.4 (6H, d, J=6 Hz), 4.2-4.6 (1H, m), 6.8 (1H, d, J=6 Hz), 7.2 (1H, d, J=10 Hz).

EXAMPLE 2

To a solution of 2-(4-chloro-2-fluoro-5-hydroxyphenyl)-5,6,7,8-tetrahydroimidazo[1,5a]pyridine-1,3(2H,8aH)-dione (1 g) in dimethylformamide (10 ml), there were added anhydrous potassium carbonate ((0.3 g) and propargyl bromide (1 g), and the mixture was stirred at 60°-70° C. for 3 hours. After allowed to cool, water was added thereto, followed by extraction with ether. The ether layer was washed with water, dried and concentrated. The residue was recrystallized from ether and petroleum ether to give 0.5 g of 2-[4-chloro-2-fluoro-5-(1-propynyloxy)phenyl]-5,6,7,8-tetrahydroimiadzo[1,5-a]pyridine-1,3(2H,8aH)-dione (Compound No. 10). M.P. 124°-125° C.

NMR (CDCl$_3$) δppm: 2.6 (1H, t, J=3 Hz), 3.0 (1H, t like m), 4.72 (2H, d, J=3 Hz), 7.0 (1H, d, J=6 Hz), 7.25 (1H, d, J=10 Hz).

EXAMPLE 3

To a solution of 2-methoxycarbonyl-4-thiomorpholine (6 g) in n-hexane (60 ml), there are added a catalytic amount of triethylamine, and 4-chloro-2-fluoro-5-methoxyphenyl isocyanate (6.9 g) was portionwise added thereto at room temperature, whereby an insoluble oily substance was solidified. After removal of n-hexane by decantation, methanol (60 ml) and a catalytic amount of sodium methoxide were added thereto, and the mixture was refluxed for 1 hour. The reaction mixture was concentrated, washed with water and extracted with ether. The ether extract was washed with water, dried over anhydrous magnesium sulfate and concentrated. The residue was purified by silica gel chromatography to give 2.6 g of 1,2-(4-chloro-2-fluoro-5-methoxyphenyl)-5,6,8,8a-tetrahydro-1H-imidazo[5,1-c][1,4]thiazine-1,3(2H)-dione (Compound No. 13). M.P. 121°-123° C.

IR ν$_{max}$ (cm$^{-1}$): 1780, 1720.

EXAMPLE 4

1,2-(4-Chloro-2-fluoro-5-methoxyphenyl)-5,6,8,8a-tetrahydro-1H-imidazo[5,1-c][1,4]thiazine-1,3(2H)-dione (1.6 g) as produced in Example 3 was dissolved in methylene chloride (30 ml), and a 70% m-chloroperbenzoic acid (2.2 g) was added thereto. The reaction was carried out at a temperature of −10°-0° C. for 6 hours. Upon confirming no presence of peracid by an iodo-starch paper, the reaction mixture was washed with sodium bicarbonate solution. The organic layer was dried over anhydrous sodium sulfate and concentrated. The residue was recrystallized from ether and petroleum ether to give 0.9 g of 1,2-(2-fluoro-4-chloro- 5-methoxyphenyl)-5,6,8,8a-tetrahydro1H-imidazo[5,1-c][1,4]thiazine-1,3(2H)-dione-7,7-oxide (Compound No. 14). M.P. 195°–196° C.

EXAMPLE 5

1,2-(2-Fluoro-4-chloro-5-hydroxyphenyl)-5,6,8,8a-tetrahydro-1H-imidazo[5,1-c][1,4]thiazine-1,3(2H)-dione-7,7-oxide (1.3 g), potassium carbonate (0.28 g) and propargyl bromide (0.5 g) were dissolved in dimethylformamide (20 ml), and the mixture was stirred at 50°–61° C. for 2.5 hours. After allowed to cool, the resultant mixture was extracted with ethyl acetate. The extract was washed with water, dried over anhydrous sodium sulfate and concentrated under reduced pressure. The residue was purified by silica gel chromatography to give 1.0 g of 1,2-(2-fluoro-4-chloro-5-propargyloxyphenyl)-5,6,8,8a-tetrahydro-1H-imidazo[5,1-c][1,4]thiazine-1,3(2H)-dione-7,7-oxide (Compound No. 25). M.P. 178°–181° C.

Examples of the hydantoin (I) produced in the same manner as above are shown in Table 1.

TABLE 1

| Compound No. | X | Y | R | Physical property |
|---|---|---|---|---|
| 1 | Cl | $CH_2$ | $-CH_3$ | M.P. 162–163° C. |
| 2 | Br | $CH_2$ | $-CH_3$ | M.P. 170.2–171.8° C. |
| 3 | Cl | $CH_2$ | $-CH_2CH_3$ | Glassy |
| 4 | Br | $CH_2$ | $-CH_2CH_3$ | M.P. 131.5–133° C. |
| 5 | Cl | $CH_2$ | $-CH_2CH_2CH_3$ | Glassy |
| 6 | Br | $CH_2$ | $-CH_2CH_2CH_3$ | Glassy |
| 7 | Cl | $CH_2$ | $-CH(CH_3)_2$ | M.P. 60.5–64.5° C. |
| 8 | Br | $CH_2$ | $-CH(CH_3)_2$ | Glassy |
| 9 | Cl | $CH_2$ | $-CH_2CH=CH_2$ | M.P. 111–112° C. |
| 10 | Cl | $CH_2$ | $-CH_2C\equiv CH$ | M.P. 124–125° C. |
| 11 | Br | $CH_2$ | $-CH_2C\equiv CH$ | M.P. 149–150° C. |
| 12 | Cl | $CH_2$ | $-(CH_2)_3CH_3$ | Glassy |
| 13 | Cl | S | $-CH_3$ | M.P. 121–123° C. |
| 14 | Cl | $SO_2$ | $-CH_3$ | M.P. 195–196° C. |
| 15 | Cl | S | $-CH_2CH_3$ | M.P. 125–126.5° C. |
| 16 | Cl | $SO_2$ | $-CH_2CH_3$ | M.P. 218–220° C. |
| 17 | Br | S | $-CH_2CH_3$ | $n_D^{24.5}$ 1.5623 |
| 18 | Br | S | $-CH_2CH_3$ | M.P. 93–94.5° C. |
| 19 | Cl | S | $-CH_2CH_2CH_3$ | $n_D^{24.0}$ 1.5540 |
| 20 | Cl | $SO_2$ | $-CH_2CH_2CH_3$ | M.P. 107–110° C. |
| 21 | Cl | S | $-CH(CH_3)_2$ | Glassy |
| 22 | Cl | $SO_2$ | $-CH(CH_3)_2$ | M.P. 69.4° C. |
| 23 | Cl | S | $-CH(CH_3)CH_2CH_3$ | M.P. 143–144° C. |
| 24 | Cl | $SO_2$ | $-CH(CH_3)CH_2CH_3$ | M.P. 154–155° C. |
| 25 | Cl | $SO_2$ | $-CH_2C\equiv CH$ | M.P. 178–181° C. |

EXAMPLE 6

A solution of 4-chloro-2-fluoro-5-isopropoxyaniline (30 g) in toluene (100 ml) was added to a 1 M phosgene/toluene solution (500 ml) at room temperature (ca. 20° C.), followed by heating under reflux. The mixture was concentrated under reduced pressure, and the residue was distilled to give 26 g of 4-chloro-2-fluoro-5-isopropoxyphenyl isocyanate as pale yellow crystals. M.P., 36°–37° C. B.P., 90°–91° C./3 mmHg.

IR $\nu_{max}$ (cm$^{-1}$): 2240.

Some examples of the phenyl isocyanate (II) produced in the same manner as above are shown in Table 2.

TABLE 2

| X | R | Physical property |
|---|---|---|
| Cl | $CH_3-$ | M.P. 42–44.5° C. |
| Cl | $n-C_3H_7-$ | M.P. 43–44° C. |
| Cl | $iso-C_3H_7-$ | M.P. 36–37° C. |
| Br | $C_2H_5-$ | M.P. 35–36.5° C. |
| Cl | $CH_2=CHCH_2-$ | B.P. 107° C./3 mmHg; $n_D^{16}$ 1.5481 |
| Cl | $CH\equiv CCH_2-$ | M.P. 61.5–62.5° C. |
| Cl | $sec-C_4H_9-$ | B.P. 102° C./1 mmHg; $n_D^{22.0}$ 1.5200 |

EXAMPLE 7

A mixture of 4-chloro-2-fluoro-5-isopropoxynitrobenzene (13.5 g) and platinum dioxide (0.4 g) in ethanol (300 ml) was subjected to catalytic reduction with hydrogen at room temperature (ca. 20° C.) under atmospheric pressure, whereby a designed amount of hydrogen was absorbed. The resultant mixture was filtered to remove insoluble materials, and the filtrate was concentrated. The residue was subjected to purification by silica gel chromatography to give 5.6 g of 4-chloro-2-fluoro-5-isopropoxyphenylaniline. $n_D^{24.5}$ 1.5360.

NMR (CDCl$_3$) δ(ppm): 1.3 (6H, d, J=6 Hz), 3.7 (2H, m, J=1.5 Hz), 4.35 (1H, q, J=6 Hz), 6.45 (1H, d, J=7 Hz), 7.1 (1H, d, J=10 Hz).

IR $\nu_{max}$ (cm$^{-1}$): 3450, 3550.

EXAMPLE 8

A suspension of electrolytic iron powder (3.5 g) in a 5% aqueous acetic acid solution (5 ml) was heated to 90° C., and a solution of 4-chloro-2-fluoro-5-(2-propynyloxy)nitrobenzene (5.7 g) in acetic acid (40 ml) was dropwise added thereto at the same temperature. The resultant mixture was stirred at 90°–105° C. for 1 hour and allowed to cool to room temperature. Water (200 ml) was added thereto. Insoluble materials were filtered off, and the filtrate was neutralized, followed by extraction with ethyl acetate. The extract was dried over anhydrous magnesium sulfate and concentrated. The residue was washed with petroleum ether and carbon tetrachloride to give 3.6 g of 4-chloro-2-fluoro-5-(2-propynyloxy)aniline. M.P. 61.0°–61.5° C.

NMR (CDCl$_3$) δ(ppm): 2.5 (1H, t, J=2 Hz), 3.4–4.2 (2H, m, J=16 Hz), 4.15 (2H, d, J=2 Hz), 6.5 (1H, d, J=8 Hz), 6.95 (1H, d, J=10 Hz).

IR $\nu_{max}$ (cm$^{-1}$): 3460, 3360, 3280, 2100.

Some examples of the aminobenzene (XII) produced in the same manner as above are shown in Table 3.

TABLE 3

| X | R | Physical property |
|---|---|---|
| Cl | $C_2H_5-$ | $n_D^{24.5}$ 1.5503 |
| Br | $C_2H_5-$ | $n_D^{25.0}$ 1.5680 |
| Cl | $n-C_3H_7-$ | $n_D^{24.5}$ 1.5386 |
| Br | $n-C_3H_7-$ | $n_D^{26.0}$ 1.5618 |
| Cl | $iso-C_3H_7-$ | $n_D^{24.5}$ 1.5360 |

TABLE 3-continued $$\underset{RO}{\overset{F}{\underset{}{\bigodot}}}\text{-NH}_2$$
with X at position ortho to RO

| X | R | Physical property |
|---|---|---|
| Br | iso-C$_3$H$_7$— | $n_D^{25.0}$ 1.5547 |
| Cl | CH$_2$=CHCH$_2$— | $n_D^{19}$ 1.5598 |
| Cl | CH≡CCH$_2$— | M.P. 61.0–61.5° C. |
| Cl | CH≡C—CH—<br>\|<br>CH$_3$ | M.P. 67.0–68° C. |

EXAMPLE 9

To a solution of 2-chloro-4-fluoro-5-nitrophenol (19.1 g) in acetonitrile (100 ml), there was added anhydrous potassium carbonate (8 g). After stirring at room temperature (ca. 20° C.) for several minutes, isopropyl iodide (25 g) was added thereto, and the resultant mixture was heated under reflux for 3 hours. After allowed to cool to room temperature (ca. 20° C.), water was added thereto, and the reaction mixture was extracted with ether. The ether extract was washed with a 5% aqueous sodium hydroxide solution and water in order, dried over anhydrous magnesium sulfate and filtered. The filtrate was concentrated under reduced pressure, and the residue was recrystallized from ethanol to give 13.5 g of 4-chloro-2-fluoro-5-isopropoxynitrobenzene. M.P., 61.3°–62.4° C.

NMR (CDCl$_3$) δ(ppm): 1.42 (6H, d, J=7 Hz), 4.3–4.8 (1H, m), 7.28 (1H, d, J=10 Hz), 7.48 (1H, d, J=6 Hz).

Some examples of the nitrobenzene (XI) produced in the same manner as above are shown in Table 4.

TABLE 4

$$\underset{RO}{\overset{F}{\underset{}{\bigodot}}}\text{-NO}_2$$

| X | R | Physical property |
|---|---|---|
| Cl | —CH$_3$ | M.P. 67.5–69.8° C. |
| Br | —CH$_3$ | M.P. 72.2° C. |
| Cl | —CH$_2$CH$_3$ | M.P. 47–48° C. |
| Br | —CH$_2$CH$_3$ | M.P. 46–46.5° C. |
| Cl | —CH$_2$CH$_2$CH$_3$ | M.P. 46–47° C. |
| Br | —CH$_2$CH$_2$CH$_3$ | M.P. 46.8–47.4° C. |
| Cl | —CH(CH$_3$)$_2$ | M.P. 61.3–62.4° C. |
| Br | —CH(CH$_3$)$_2$ | M.P. 65.5–66.5° C. |
| Cl | —CH(CH$_3$)CH$_2$CH$_3$ | M.P. 59.6–60.6° C. |
| Cl | —CH$_2$CH=CH$_2$ | $n_D^{17.0}$ 1.5601 |
| Cl | —CHCH=CH$_2$<br>\|<br>CH$_3$ | M.P. 41.0–41.5° C. |
| Cl | —CH$_2$C≡CH | M.P. 88–89° C. |
| Cl | —CHC≡CH<br>\|<br>CH$_3$ | M.P. 87–88° C. |

EXAMPLE 10

2-Chloro-4-fluorophenol (83.4 g) was added to a solution of sodium hydroxide (27.7 g) in water (450 ml), and methyl chloroformate (69.2 g) was dropwise added thereto at a temperature below 10° C. Precipitated crystals were collected by filtration and washed with water to give methyl (2-chloro-4-fluorophenyl)formate (134.8 g). M.P., 69°–71° C.

Methyl (2-chloro-4-fluorophehyl)formate (134.8 g) obtained above was suspended in conc. sulfuric acid (50 ml). To the suspension, a mixture of conc. sulfuric acid (50 ml) and conc. nitric acid (50 ml) was added at about 30° C., and the mixture was stirred at this temperature for 1 hour. The reaction mixture was poured into ice water, and precipitated crystals were collected and washed with water to give methyl (2-chloro-4-fluoro-5-nitrophenyl)formate (143 g). M.P., 50°–55° C.

The product obtained as above was combined with sodium hydroxide (27 g) and water (300 ml), and the resultant mixture was refluxed for 4 hours. Precipitated insoluble materials were filtered using a celite, and the filtrate was acidified with conc. hydrochloric acid. Precipitated crystals were collected by filtration and washed with water to obtain 76.3 g of 2-chloro-4-fluoro-5-nitrophenol. M.P., 106°–107° C.

NMR (CDCl$_3$, D$_6$-DMSO) δ(ppm): 7.25 (1H, d, J=10 Hz), 7.64 (1H, d, J=6 Hz).

IR $\nu_{max}^{nujol}$ (cm$^{-1}$): 3370.

EXAMPLE 11

To a solution of 2-bromo-4-fluorophenol (28 g) in a solution of sodium hydroxide (7 g) in water (100 ml), methyl chloroformate was dropwise added thereto at a temperature below 10° C. The produced crystals were collected by filtration and washed with water to give methyl 2-bromo-4-fluorophenylformate (41 g). M.P., 80.7° C.

The above product was suspended in conc. sulfuric acid (13 ml), a mixture of conc. sulfuric acid (13 ml) and conc. nitric acid (13 ml) was dropwise added thereto at about 30° C., and the resultant mixture of stirred for 30 minutes. The reaction mixture was poured into ice water. The produced crystals were collected by filtration and washed with water to give methyl 2-bromo-4-fluoro-5-nitroformate (38.3 g) as yellow crystals. M.P., 63.5°–64.5° C.

The thus obtained product was admixed with sodium hydroxide (6.2 g) and water (100 ml) and heated under reflux for 3 hours. The insoluble materials were eliminated by filtration, and the filtrate was acidified with hydrochloric acid. The precipitated crystals were collected by filtration and washed with water to give 25 g of 2-bromo-4-fluoro-5-nitrophenol. M.P., 126°–127° C.

NMR (CDCl$_3$, D$_6$-DMSO) δ(ppm): 7.42 (1H, d, J=10 Hz), 7.65 (1H, d, J=6 Hz).

IR $\nu_{max}^{nujol}$ (cm$^{-1}$): 3450.

EXAMPLE 12

4-Bromo-2-fluoro-5-hydroxyphenyl isocyanate (3 g) was dissolved in chlorobenzene (5 ml), and a solution of pipecolic acid (1.7 g) and sodium hydroxide (0.56 g) in water (5 ml) was added thereto, followed by stirring at room temperature (ca. 20° C.) overnight. The aqueous layer was washed with ether, made acidic with an aqueous hydrochloric acid solution and heated under reflux for 2 hours. After allowed to cool, the resulting mixture was extracted with methylene chloride (300 ml). The extract was washed with sodium bicarbonate solution, dried and concentrated. The residue was recrystallized from ether to give 1.75 g of 2-(4-bromo-2-fluoro-5-hydroxyphenyl)-5,6,7,8-tetrahydroimidazo[1,5-a]pyridine-1,3(2H,8aH)-dione. M.P., 196°–199° C.

IR $\nu_{max}$ (cm$^{-1}$): 3400, 1760, 1700.

Some examples of the hydroxyhydantoin (V) produced in the same manner as above are shown in Table 5.

TABLE 5

| X | Y | Physical property |
|---|---|---|
| Cl | —CH$_2$— | M.P. 193.5–194° C. |
| Br | —CH$_2$— | M.P. 196–199° C. |
| Cl | —S— | M.P. 207.5–209.5° C. |
| Cl | —SO$_2$— | Glassy |

EXAMPLE 13

Ethyl pipecolate hydrochloride (4.64 g) was treated with a 1% sodium hydroxide solution (100 ml), followed by extraction with toluene. The toluene layer was washed with a saturated sodium chloride solution, 4-chloro-2-fluoro-(1-methylethoxy)phenyl isocyanate (5 g) was dropwise added thereto, and the resultant mixture was stirred for 4 hours. Toluene was removed under reduced pressure to give 5.93 g of ethyl N-[4-chloro-2-fluoro-5-(1-methylethoxy)phenylcarbamoyl]-pipecolate as a glassy substance.

NMR (CDCl$_3$) δ ppm: 1.25 (3H, t), 1.32 (6H, d), 4.2 (2H, q), 7.82 (1H, d).

Some examples of the urea (IV) produced in the same manner as above are shown in Table 6.

TABLE 6

| X | Y | R | R' | Physical property |
|---|---|---|---|---|
| Cl | CH$_2$ | iso-C$_3$H$_7$ | Na | M.P. 59.5–65° C. |
| Cl | CH$_2$ | iao-C$_3$H$_7$ | C$_2$H$_5$ | Glassy |
| Cl | S | iso-C$_3$H$_7$ | C$_2$H$_5$ | M.P. 114–116° C. |

In the practical usage of the hydantoins (I), they may be applied as such or in any preparation form such as dusts, granules, wettable powders, emulsifiable concentrates or suspensions.

The concentration of the active ingredient in such preparation form is usually within a range of 0.1 to 80% by weight. However, the upper and lower range may be also effective depending upon purposes.

For formulation of those preparations, a solid or liquid carrier or diluent may be used. As the solid carrier or diluent, there may be employed mineral powders (e.g. kaolin, bentonite, montmorillonite, talc, diatomaceous earth, mica, vermiculite, gypsum, calcium carbonate, apatite, synthetic hydrous silicate), vegetable powders (e.g. soybean powder, wheat flour, wooden powder, tobacco powder, starch, crystalline cellulose), high molecular weight compounds (e.g. petroleum resin, polyvinyl chloride, dammar gum, ketone resin), alumina, wax, etc.

As the liquid carrier or diluent, there may be employed alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water, etc.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. If necessary, gelatin, casein, sodium alginate, starch, agar, polyvinyl alcohol, ligninsulfonates, isopropyl acid phosphate or the like may be used as an auxiliary agent.

The hydantoins (I) of the invention may be used together with other herbicides to improve their activity as herbicides, and in some cases, a synergistic effect can be expected. As the other herbicides, there may be exemplified phenoxy series herbicides such as 2,4-dichlorophenoxyacetic acid, 2-methyl-4-chlorophenoxybutyric acid and 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine and 4-amino-6-t-butyl-3-methylthio-1,2,4-triazin-5-one; urea series herbicides such as 3-(3,4-dichlorophenyl)-1,1-dimethylurea, 3-(3,4-dichlorophenyl)-1-methoxy-1-methylurea, 1-(2,2-dimethylbenzyl)-3-p-tolylurea and 1,1-dimethyl-3-(3-trifluoromethylphenyl)urea; carbamate series herbicides such as isopropyl N-(3-chlorophenyl)carbamate and methyl N-(3,4-dichlorophenyl)carbamate; thiolcarbamate series herbicides such as S-(4-chlorobenzyl)-N,N-diethylthiolcarbamate, S-ethyl-N,N-hexamethylenethiolcarbamate, S-ethyl-N,N-diisobutylthiolcarbamate, S-ethyl-N,N-di-n-propylthiolcarbamate and S-n-propyl-N,N-di-n-propylthiolcarbamate; anilide series herbicides such as 3,4-dichloropropionanilide, N-methoxymethyl-2,6-diethyl-α-chloroacetanilide, 2-chloro-2',6'-diethyl-N-(butoxymethyl)acetanilide, 2-chloro-2',6'-diethyl-N-(n-propoxyethyl)acetanilide, N-chloroacetyl-N-(2,6-diethylphenyl)glycine ethyl ether and 2-chloro-N-(2-ethyl-6-methylphenyl)-N-(2-methoxy-1-methyl)acetamide; uracil series herbicides such as 5-bromo-3-sec-butyl-6-methyluracil and 3-cyclohexyl-5,6-trimethyleneuracil; pyridinium chloride series herbicide such as 1,1'-dimethyl-4,4-bispyridinium chloride; phosphate series herbicides such as N,N-bis(-phosphonomethyl)glycine, O-ethyl-O-(2-nitro-5-methylphenyl)-N-sec-butylphosphoroamidothioate, S-(2-methyl-1-pyperidylcarbonylmethyl)-O,O-di-n-propyldithiophosphate and S-(2-methyl-1-pyperidylcarbonylmethyl)-O,O-diphenyldithiophosphate; toluidine series herbicide such as α,α,α-trifluoro-2,6-dinitro-N,N-dipropyl-p-toluidine; 5-t-butyl-3-(2,4-dichloro-5-isopropoxyphenyl)-1,3,4-oxadiazolin-2-one; 3-isopropyl-1H-2,1,3-benzothiadiazin-(4)-3H-one-2,2-dioxide; α-(β-naphthoxy)propionanilide; 4-(2,4-dichlorobenzoyl)-1,3-dimethylpyrazol-5-yl-p-toluenesulfonate; 4'-phenylsulfonyl-1,1,1-trifluorosulfono-o-toluidide; 4-chloro-5-methylamino-2-(3-trifluoromethylphenyl)pyridazin-3(2H)-one; 1-methyl-3-phenyl-5-(3-trifluoromethylphenyl)pyridin-4(1H)-one; 2-methyl-4-phenylsulfonyl-trifluoromethylsulfoanilide; 2-(3,4-dichlorophenyl)-4-methyltetrahydro-1,2,4-oxadiazol-3,5-dione; 4-chloro-5-methylamino-2-(3-trifluoromethylphenyl)pyridazin-3(2H)-one; etc. However, the herbicides are not limited to these examples. Further, they may be also applied in combination with insecticides, nematocides, fungicides, plant growth regulators, fertilizers, etc.

Practical embodiments of the herbicidal composition according to the invention are illustratively shown in the following examples wherein parts and % are by weight. The compound number of the active ingredient corresponds to the one in Table 1.

PREPARATION EXAMPLE 1

Eighty parts of Compound No. 13, 3 parts of alkylsulfate, 2 parts of ligninsulfonate and 15 parts of hydrous silica are well mixed while being powdered to obtain a wettable powder.

PREPARATION EXAMPLE 2

Ten parts of Compound No. 22, 3 parts of alkylarylsulfate, 7 parts of polyoxyethylene alkylaryl ether, 60 parts of cyclohexanone and 20 parts of xylene are well mixed while being powdered to obtain an emulsifiable concentrate.

PREPARATION EXAMPLE 3

0.1 Part of Compound No. 23, 1 part of hydrous silica, 35 parts of bentonite and 63.9 parts of kaolin are well mixed while being powdered. The mixture is then kneaded with water, granulated and dried to obtain granules.

PREPARATION EXAMPLE 4

Three parts of Compound No. 16, 0.3 part of isopropyl acid phosphate, 66.7 parts of kaolin and 30 parts of talc are well mixed while being powdered to obtain a dust.

PREPARATION EXAMPLE 5

Twenty parts of Compound No. 25 is mixed with 60 parts of an aqueous solution containing 3% polyoxyethylene sorbitan monolaurate and pulverized until the particle size of the active ingredient becomes less than 3 microns. Twenty parts of an aqueous solution containing 3% of sodium alginate as a dispersing agent are incorporated therein to obtain a suspension.

The dosage rate of the hydantoins (I) may vary on their kinds, the sorts of cultivated plants, the modes of application, etc. Generally, however, the dosage rate is from 0.05 to 50 grams, preferably from 0.1 to 20 grams, of the active ingredient per are.

The application of the hydantoins (I) as herbicides will be illustratively shown in the following Examples wherein the phytotoxicity to crop plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity and the herbicidal activity were evaluated by the standard given in the table below. The rating values of phytotoxicity, 0 and 1, and those of herbicidal effect, 5 and 4, are generally regarded as satisfactory to protect crop plants and to control weeds, respectively. The rating values in the paddy field test alone were calculated from the dry weight of the test plants.

| Rating value | Fresh weight (percentage to untreated plot) (%) | |
|---|---|---|
| | Crop plant | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following compounds were used in the Examples for comparison:

| Compound No. | Structure | Remarks |
|---|---|---|
| (a) | [structure: 4-chlorophenyl hydantoin fused with piperidine] | British Patent 1,503,244 |
| (b) | [structure: 4-chloro-2-fluorophenyl hydantoin fused with piperidine] | U.S. Pat. No. 3,958,976 |

-continued

| Compound No. | Structure | Remarks |
|---|---|---|
| (c) | [structure: 4-chloro-2-fluorophenyl with thiomorpholine dione] | U.S. Pat. No. 4,179,276 |
| (d) | [structure: 4-chloro-2-fluorophenyl with SO₂-containing ring dione] | U.S. Pat. No. 4,179,276 |
| (e) | [structure: triazine with Cl, NHCH(CH₃)₂, NHC₂H₅] | Commercially available herbicide known as "Atrazine" |
| (f) | [structure: NC-C₆H₂(I)₂-OH] | Commercially available herbicide known as "Ioxynil" |
| (g) | [structure: F₃C-C₆H₃(Cl)-O-C₆H₃(OCH₃)-NO₂] | Commercially available herbicide known as "Chlormethoxynil" |
| (h) | [structure: 2,6-diethylphenyl-N(CH₂OCH₃)-COCH₂Cl] | Commercially available herbicide known as "Alachlor" |
| (i) | HOOCCH₂NHCH₂P(O)(OH)₂ | Commercially available herbicide known as "Glyphosate" |

TEST EXAMPLE 1

Plastic beakers (diameter, 10 cm; height, 10 cm) were filled with upland field soil, and the seeds of barnyardgrass, wild oat, tall morningglory and velvetleaf were separately sowed in the beakers. A designed amount of the test compound formulated into an emulsifiable concentrate according to Preparation Example 2 and dispersed in water was sprayed over the top by means of a small hand sprayer at a spray volume of 5 liters per are. After the spraying, the test plants were grown for 20 days in the greenhouse, and herbicidal activity was examined. The results are shown in Table 7.

TABLE 7

| Compound No. | Dosage (weight of active ingredient, g/are) | Herbicidal activity | | | |
|---|---|---|---|---|---|
| | | Barn-yard-grass | Wild oat | Tall morning-glory | Velvet-leaf |
| 1 | 5 | 5 | 5 | 5 | 5 |
| | 2.5 | 5 | 5 | 4 | 5 |
| 2 | 5 | 5 | 5 | 5 | 5 |
| | 2.5 | 5 | 5 | 4 | 5 |
| 3 | 5 | 5 | 5 | 5 | 5 |
| | 2.5 | 5 | 5 | 4 | 5 |
| 4 | 5 | 5 | 5 | 5 | 5 |
| | 2.5 | 5 | 5 | 4 | 5 |
| 5 | 5 | 5 | 5 | 5 | 5 |
| | 2.5 | 5 | 5 | 4 | 5 |
| 6 | 5 | 5 | 5 | 5 | 5 |
| | 2.5 | 5 | 5 | 4 | 5 |
| 7 | 5 | 5 | 5 | 5 | 5 |
| | 2.5 | 5 | 5 | 5 | 5 |
| 8 | 5 | 5 | 5 | 5 | 5 |
| | 2.5 | 5 | 5 | 5 | 5 |
| 9 | 5 | 5 | 5 | 5 | 5 |
| | 2.5 | 5 | 5 | 4 | 5 |

TABLE 7-continued

| Compound No. | Dosage (weight of active ingredient, g/are) | Herbicidal activity | | | |
|---|---|---|---|---|---|
| | | Barnyard-grass | Wild oat | Tall morning-glory | Velvet-leaf |
| 12 | 5 | 5 | 5 | 5 | 5 |
| | 2.5 | 5 | 5 | 4 | 5 |
| (a) | 5 | 0 | 1 | 0 | 2 |
| | 2.5 | 0 | 0 | 0 | 0 |
| (b) | 5 | 3 | 1 | 0 | 5 |
| | 2.5 | 0 | 0 | 0 | 2 |

TEST EXAMPLE 2

Plastic beakers (diameter, 10 cm; height, 10 cm) were filled with upland field soil, and the seeds of barnyardgrass, wild oat, tall morningglory and velvetleaf and seeds of soybean and cotton were separately sowed in the beakers. A designed amount of the test compound formulated into an emusifiable concentrate according to Preparation Example 2 and dispersed in water was sprayed over the top by means of a small hand sprayer at a spray volume of 5 liters per are. After the spraying, the test plants were grown for 20 days in the greenhouse, and herbicidal activity and phytotoxicity were examined. The results are shown in Table 8.

TABLE 8

| Compound No. | Dosage (weight of active ingredient, g/are) | Herbicidal activity | | | | Phytotoxicity | |
|---|---|---|---|---|---|---|---|
| | | Barn-yard-grass | Wild oat | Tall morning-glory | Vel-vet-leaf | Soy-bean | Cot-ton |
| 10 | 1.25 | 5 | 5 | 5 | 5 | — | — |
| | 0.63 | 5 | 4 | 4 | 5 | 1 | — |
| 11 | 1.25 | 5 | 5 | 5 | 5 | 0 | — |
| 13 | 1.25 | 4 | 4 | 4 | 5 | 1 | — |
| 14 | 1.25 | 5 | 5 | 5 | 5 | — | — |
| | 0.63 | 4 | 4 | 4 | 5 | 1 | — |
| 15 | 1.25 | 5 | 4 | 4 | 5 | 1 | — |
| 16 | 1.25 | 5 | 5 | 5 | 5 | — | — |
| | 0.63 | 5 | 4 | 4 | 5 | 1 | 1 |
| 17 | 1.25 | 5 | — | 4 | 5 | 0 | — |
| 18 | 1.25 | 5 | 4 | 4 | 5 | — | — |
| | 0.63 | 5 | — | — | 5 | 0 | 0 |
| 19 | 1.25 | 5 | 5 | 5 | 5 | — | — |
| 20 | 1.25 | 5 | 5 | 4 | 5 | — | — |
| | 0.63 | 4 | 4 | — | 5 | 1 | 1 |
| 21 | 1.25 | 5 | 5 | 5 | 5 | 1 | 2 |
| | 0.63 | 5 | 4 | 4 | 5 | 0 | 0 |
| 22 | 1.25 | 5 | 5 | 5 | 5 | 0 | 0 |
| | 0.63 | 5 | 5 | 5 | 5 | 0 | 0 |
| 23 | 1.25 | 5 | 5 | 4 | 5 | 1 | — |
| 24 | 1.25 | 5 | 5 | 4 | 5 | — | — |
| | 0.63 | 4 | 4 | — | 5 | 0 | 0 |
| 25 | 1.25 | 5 | 4 | 5 | 5 | — | — |
| | 0.63 | 5 | 4 | — | 5 | 0 | — |
| (c) | 1.25 | 2 | 1 | 2 | 3 | 2 | 1 |
| (d) | 1.25 | 4 | 3 | 3 | 4 | 3 | 3 |

TEST EXAMPLE 3

Plastic beakers (diameter, 10 cm; height, 10 cm) were filled with upland field soil, and the seeds of barnyardgrass, wild oat, wild mustard and velvetleaf were separately sowed in the beakers and grown for 2 weeks in a greenhouse. A designed amount of the test compound was sprayed to the foliage of the test plants by means of a small hand sprayer. After the spraying, the test plants were further grown for 3 weeks in the greenhouse, and herbicidal activity was examined. The results are shown in Table 9. In this treatment, the test compound was formulated into an emusifiable concentrate according to Preparation Example 2 and applied at a spray volume of 5 liters per are by dispersing it in water with the addition of a spreading agent.

TABLE 9

| Compound No. | Dosage (weight of active ingredient, g/are) | Herbicidal activity | | | |
|---|---|---|---|---|---|
| | | Barnyard-grass | Wild oat | Wild mustard | Velvet-leaf |
| 1 | 1.25 | 4 | 4 | 5 | 5 |
| 2 | 5 | 4 | 4 | 5 | 5 |
| 3 | 1.25 | 5 | 5 | 5 | 5 |
| 4 | 1.25 | 4 | 3 | 4 | 5 |
| 6 | 5 | 4 | 4 | 5 | 5 |
| 7 | 1.25 | 5 | 5 | 5 | 5 |
| 8 | 5 | 4 | 4 | 5 | 5 |
| 13 | 1.25 | 4 | 5 | 5 | 5 |
| 14 | 1.25 | 3 | 5 | 5 | 5 |
| 15 | 1.25 | 4 | 4 | 5 | 5 |
| 16 | 1.25 | 5 | 4 | 5 | 5 |
| 18 | 1.25 | 4 | 4 | 5 | 5 |
| 19 | 1.25 | 4 | 3 | 5 | 5 |
| 20 | 1.25 | 3 | 3 | 4 | 5 |
| 22 | 1.25 | 4 | 5 | 5 | 5 |
| (a) | 5 | 0 | 0 | 0 | 5 |
| | 1.25 | 0 | 0 | 0 | 3 |
| (b) | 5 | 2 | 3 | 4 | 5 |
| | 1.25 | 0 | 1 | 0 | 3 |
| (c) | 1.25 | 0 | 0 | 1 | 4 |
| (d) | 1.25 | 1 | 1 | 2 | 5 |

TEST EXAMPLE 4

Plastic trays (35 cm×25 cm×15 cm) were filled with upland field soil, and the seeds of tall morningglory, velvetleaf, prickly sida, jimsonweed, black nightshade, redroot pigweed, Johnsongrass and green foxtail, and the seeds of cotton and soybean were sowed therein. A designed amount of the test compound formulated into a wettable powder according to Preparation Example 1 and dispersed in water was sprayed over the top by means of a small hand sprayer at a spray volume of 5 liters per are. After the spraying, the test plants were grown in a greenhouse for 20 days, and phytotoxicity and herbicidal activity were examined. The results are shown in Table 10.

TABLE 10

| Compound No. | Dosage (weight of active ingredient, g/are) | Herbicidal activity | | | | | | | | Phytotoxicity | |
|---|---|---|---|---|---|---|---|---|---|---|---|
| | | Tall morning-glory | Velvet-leaf | Prickly sida | Jimson-weed | Black night-shade | Redroot pigweed | Johnson-grass | Green foxtail | Cotton | Soybean |
| 1 | 10 | 4 | 5 | 5 | 5 | 5 | 5 | 5 | 5 | 1 | 0 |
| | 5 | 4 | 5 | 5 | 5 | 5 | 5 | 5 | 5 | 0 | 0 |
| 2 | 10 | 5 | 5 | 5 | 5 | 5 | 5 | 5 | 5 | — | 1 |
| | 5 | 4 | 5 | 5 | 5 | 5 | 5 | 4 | 5 | 1 | 0 |
| 3 | 10 | 5 | 5 | 5 | 5 | 5 | 5 | 5 | 5 | 1 | 1 |
| | 5 | 4 | 5 | 5 | 5 | 5 | 5 | 5 | 5 | 0 | 1 |
| 4 | 5 | 5 | 5 | 5 | 5 | 5 | 5 | 5 | 5 | 1 | 0 |

TABLE 10-continued

| Compound No. | Dosage (weight of active ingredient, g/are) | Herbicidal activity | | | | | | | | Phytotoxicity | |
|---|---|---|---|---|---|---|---|---|---|---|---|
| | | Tall morningglory | Velvetleaf | Prickly sida | Jimsonweed | Black nightshade | Redroot pigweed | Johnsongrass | Green foxtail | Cotton | Soybean |
| 5 | 10 | 4 | 5 | 5 | 5 | 5 | 5 | 5 | 5 | 0 | 0 |
|   | 5  | — | 5 | 5 | 5 | 5 | 5 | — | 5 | 0 | 0 |
| 6 | 10 | 5 | 5 | 5 | 5 | 5 | 5 | 5 | 5 | 0 | 1 |
|   | 5  | 4 | 5 | 5 | 5 | 5 | 5 | 5 | 5 | 0 | 0 |
| 7 | 10 | 5 | 5 | 5 | 5 | 5 | 5 | 5 | 5 | 1 | 1 |
|   | 5  | 4 | 5 | 5 | 5 | 5 | 5 | 4 | 5 | 1 | 1 |
| 8 | 5  | 5 | 5 | 5 | 5 | 5 | 5 | 5 | 5 | 1 | — |
| 9 | 10 | 5 | 5 | 5 | 5 | 5 | 5 | 5 | 5 | — | — |
|   | 5  | 4 | 5 | 5 | 5 | 5 | 5 | — | 5 | 0 | 0 |
| 12| 10 | 4 | 5 | 5 | 5 | 5 | 5 | 4 | 5 | 0 | 0 |
|   | 5  | — | 5 | 5 | 5 | 5 | 5 | — | 5 | 0 | 0 |
| (a)| 10| 0 | 3 | 2 | 1 | 3 | 5 | 1 | 2 | 1 | 0 |
| (b)| 10| 1 | 4 | 4 | 3 | 5 | 5 | 3 | 4 | 1 | 1 |
|    | 5 | 0 | 3 | 4 | 2 | 4 | 5 | 2 | 2 | 1 | 0 |
| (h)| 20| 1 | 0 | 2 | 0 | 4 | 5 | 2 | 5 | 0 | 0 |

TEST EXAMPLE 5

Plastic trays (35 cm × 25 cm × 15 cm) were filled with upland field soil, and the seeds of corn, wheat, velvetleaf, cocklebur, tall morningglory, common lambsquarters, black nightshade and green foxtail were sowed and grown for 2 to 3 weeks in a greenhouse. Every two trays were placed in a frame (50 cm × 100 cm × 40 cm) and a designed amount of the test compound was sprayed thereover by means of a small hand sprayer. The test plants were further grown for 3 weeks in the greenhouse and herbicidal activity and phytotoxicity were examined. The results are shown in Table 11. In this treatment, the test compound was formulated into an emulsifiable concentrate according to Preparation Example 2 and applied by diluting it in water (25 liters) with the addition of a spreading agaent. At the time of application, the plants were generally at the 1 to 4 leaf stage and in 1.5 to 20 cm height.

TEST EXAMPLE 6

Seeds of cocklebur, common purslane, tall morningglory, jimsonweed, sicklepod and velvetleaf and the seeds of corn were sowed to the depth of 3 cm of the plotted field each having 3 m². Eighteen days thereafter and at the time when the corn grew up to the 6-leaf stage and in 40 cm height and the weeds were at 2 to 4-leaf stages and in 5 to 15 cm height, a designed amount of the test compound was sprayed to the test plants with three replications over the top by means of a small hand sprayer. After cultivation for additional 18 days, herbicidal activity and phytotoxicity were examined. The results are shown in Table 12. In this treatment, the test compound of the invention was formulated into an emulsifiable concentrate according to Preparation Example 2 whereas that for comparison was a commercially available wettable powder. Both compounds were diluted with water containing a spreading agent and applied at a spray volume of 150 ml per plot.

TABLE 11

| Compound No. | Dosage (weight of active ingredient, g/are) | Phytotoxicity | | Herbicidal activity | | | | | |
|---|---|---|---|---|---|---|---|---|---|
| | | Corn | Wheat | Velvetleaf | Cocklebur | Tall morningglory | Common lambsquarters | Black nightshade | Green foxtail |
| 3 | 0.63 | — | — | 5 | 5 | 5 | 5 | 5 | 4 |
|   | 0.32 | 1 | 1 | 5 | 5 | 5 | 5 | 5 | 2 |
|   | 0.16 | 0 | 1 | 5 | 5 | 4 | 5 | 5 | 1 |
| 4 | 0.63 | — | — | 5 | 5 | 5 | 5 | 5 | 3 |
|   | 0.32 | 1 | 1 | 5 | 5 | 4 | 5 | 5 | 2 |
| 7 | 0.63 | 1 | 1 | 5 | 5 | 5 | 5 | 5 | 4 |
|   | 0.32 | 1 | 1 | 5 | 5 | 5 | 5 | 5 | 3 |
|   | 0.16 | 0 | 1 | 5 | 5 | 5 | 5 | 5 | 2 |
| 8 | 0.63 | — | — | 5 | 5 | 5 | 5 | 5 | 4 |
|   | 0.32 | 1 | 1 | 5 | 5 | 5 | 5 | 5 | 3 |
| 15| 0.63 | 1 | 1 | 5 | 5 | 5 | 5 | 5 | 4 |
|   | 0.32 | 0 | 0 | 5 | 5 | 5 | 5 | 5 | 2 |
| 19| 0.63 | 1 | 0 | 5 | 5 | 5 | 5 | 5 | 4 |
|   | 0.32 | 0 | 0 | 5 | 5 | 5 | 5 | 4 | 3 |
| 22| 0.63 | 0 | 1 | 5 | 5 | 5 | 5 | 5 | 5 |
|   | 0.32 | 0 | 1 | 5 | 5 | 5 | 5 | 5 | 3 |
| 25| 0.63 | 1 | 1 | 5 | 5 | 5 | 5 | 5 | 4 |
|   | 0.32 | 0 | 0 | 5 | 5 | 5 | 5 | 5 | 2 |
| (c)| 0.63 | 1 | 1 | 5 | 4 | 3 | 3 | 2 | 1 |
|    | 0.32 | 1 | 0 | 3 | 2 | 2 | 2 | 1 | 1 |
| (d)| 0.63 | 1 | 1 | 5 | 4 | 4 | 5 | 2 | 1 |
|    | 0.32 | 1 | 0 | 3 | 3 | 3 | 3 | 2 | 1 |
| (e)| 0.63 | 0 | — | 5 | 5 | 5 | — | — | 1 |
|    | 0.32 | 0 | — | 4 | 3 | 3 | — | — | 0 |

TABLE 12

| Compound No. | Dosage (weight of active ingredient, g/are) | Phytotoxicity Corn | Herbicidal activity |  |  |  |  |  |
|---|---|---|---|---|---|---|---|---|
| | | | Cocklebur | Common purslane | Tall morning-glory | Jimsonweed | Sicklepod | Velvetleaf |
| 22 | 0.63 | 0 | 5 | 5 | 5 | 5 | 5 | 5 |
| | 0.32 | 0 | 5 | 5 | 4 | 5 | 4 | 5 |
| | 0.16 | 0 | 4 | 5 | 3 | 5 | 4 | 4 |
| (e) | 10 | 0 | 5 | 5 | 4 | 5 | 3 | 5 |
| | 5 | 0 | 5 | 5 | 3 | 5 | 2 | 4 |
| | 2.5 | 0 | 3 | 4 | 2 | 5 | 1 | 2 |

TEST EXAMPLE 7

In a plastic pot (10 cm in diameter), upland soil was filled, and tubers of purple nutsedge (Cyperus rotundus) were transplanted at the depth of 2 cm from the soil surface and cultivated in a greenhouse for 4 weeks, whereby purple nutsedge was in 7-leaved stage. A designed amount of the test compound formulated into an emulsifiable concentrate according to Preparation Example 2 and diluted with water was applied to the foliage of the test plant by means of a hand sprayer, and the test plants were further grown in the greenhouse for 8 weeks and subjected to observation by removal of the soil with water. The herbicidal activity on the aerial part (e.g. leaves) and the underground part (e.g. rhizome and tuber) was evaluated according to the same criteria as in Test Example 1. The results are shown in Table 13.

TABLE 13

| Compound No. | Dosage of (weight of active ingredient, g/are) | Herbicidal activity | |
|---|---|---|---|
| | | Aerial part | Underground part |
| 1 | 20 | 5 | 5 |
| | 10 | 4 | 4 |
| 3 | 20 | 5 | 4 |
| | 10 | 5 | 4 |
| 4 | 20 | 5 | 4 |
| | 10 | 5 | 4 |
| 7 | 20 | 5 | 4 |
| | 10 | 5 | 4 |
| 8 | 20 | 5 | 4 |
| | 10 | 5 | 4 |
| 14 | 20 | 5 | 5 |
| | 10 | 5 | 4 |
| 15 | 20 | 5 | 4 |
| | 10 | 5 | 4 |
| 22 | 20 | 5 | 4 |
| | 10 | 5 | 4 |
| (a) | 40 | 2 | 0 |
| (b) | 40 | 2 | 1 |
| (c) | 10 | 1 | 0 |
| (i) | 40 | 5 | 4 |
| | 20 | 4 | 4 |

TEST EXAMPLE 8

Wagner's pots (1/5000 are) were filled with paddy field soil and the seeds of annual weeds (e.g. barnyardgrass, monochoria, broad-leaved weeds) were sowed to 2 to 3 cm depth, and water was poured therein until the depth of water became 4 cm. Rice seedlings of the 4-leaf stage and the tubers or buds of perenial weeds (e.g. slender spikerush, hardstem bulrush, arrowhead) were transplanted therein and grown for 5 days. At the time when the germination occurred, a desinged amount of the test compound formulated in an emulsifiable concentrate according to Preparation Example 2 was applied to the pots by perfusion. Thereafter, the test plants were grown for further 4 weeks and herbicidal activity and phytotoxicity were examined. The results are shown in Table 14.

TABLE 14

| Compound No. | Dosage (weight of active ingredient, g/are) | Herbicidal activity | | | | | Phytotoxicity |
|---|---|---|---|---|---|---|---|
| | | Barnyardgrass | Monochoria | Broad-leaved weed | Slender spikerush | Hardstem bulrush | Arrowhead | Rice plant |
| 6 | 0.5 | 5 | 5 | 5 | 5 | 4 | 4 | 0 |
| | 0.25 | 4 | 5 | 5 | 5 | 5 | 3 | 0 |
| 7 | 0.5 | 5 | 5 | 5 | 5 | 5 | 5 | 0 |
| | 0.25 | 3 | 5 | 5 | 4 | 4 | 4 | 0 |
| 8 | 0.5 | 5 | 5 | 5 | 5 | 5 | 5 | 0 |
| | 0.25 | 3 | 5 | 5 | 4 | 4 | 4 | 0 |
| 13 | 0.5 | 3 | 5 | 5 | 5 | 4 | 5 | — |
| | 0.25 | 3 | 5 | 5 | 4 | 4 | 4 | — |
| 23 | 0.5 | 5 | 5 | 5 | 4 | 4 | 4 | — |
| | 0.25 | 4 | 5 | 5 | 4 | 3 | 4 | — |
| (a) | 0.5 | 1 | 3 | 3 | 1 | 1 | 1 | 0 |
| | 0.25 | 1 | 2 | 2 | 1 | 0 | 0 | 0 |
| (b) | 0.5 | 2 | 3 | 3 | 2 | 1 | 1 | 0 |
| | 0.25 | 1 | 2 | 3 | 1 | 1 | 0 | 0 |
| (d) | 0.5 | 1 | 2 | 2 | 2 | 1 | 0 | — |
| | 0.25 | 0 | 2 | 2 | 1 | 1 | 0 | — |
| (g) | 0.5 | 2 | 2 | 2 | 2 | 1 | 1 | 0 |

| Compound No. | Dosage (weight of active ingredient, g/are) | Herbicidal activity | | | | | Phytotoxicity |
| --- | --- | --- | --- | --- | --- | --- | --- |
| | | Barnyard-grass | Monochoria | Broad-leaved weed | Slender spikerush | Hardstem bulrush | Arrow-head | Rice plant |
| | 0.25 | 1 | 2 | 2 | 1 | 0 | 0 | 0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compound of the formula:

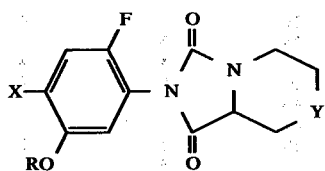

wherein X is a chlorine atom or a bromine atom, Y is —CH$_2$—, —S— or —SO$_2$— and R is a C$_1$-C$_4$ alkyl group, an allyl group or a propargyl group.

2. 2-(4-Chloro-2-fluoro-5-methoxyphenyl)-5,6,7,8-tetrahydroimidazo[1,5-a]pyridine-1,3(2H,8aH)-dione.

3. 2-(4-Bromo-2-fluoro-5-methoxyphenyl)-5,6,7,8-tetrahydroimidazo[1,5-a]pyridine-1,3(2H,8aH)-dione.

4. 2-(4-Chloro-2-fluoro-5-propoxyphenyl)-5,6,7,8-tetrahydroimidazo[1,5-a]pyridine-1,3(2H,8aH)-dione.

5. 2-(4-Chloro-2-fluoro-5-(1-methylethoxy)phenyl-5,6,7,8-tetrahydroimidazo[1,5-a]pyridine-1,3(2H,8aH)-dione.

6. 2-(4-Chloro-2-fluoro-5-methoxyphenyl)-5,6,7,8-tetrahydro-1H-imidazo[5,1-c][1,4]thiazine-1,3(2H)-dione-7,7-dioxide.

7. 2-(4-Chloro-2-fluoro-5-ethoxyphenyl)-5,6,7,8-tetrahydro-1H-imidazo[5,1-c][1,4]thiazine-1,3(2H)-dione-7,7-dioxide.

8. 2-(4-Chloro-2-fluoro-5-(1-methylethoxy)phenyl-5,6,7,8-tetrahydro-1H-imidazo[5,1-c][1,4]thiazine-1,3(2H)-dione-7,7-dioxide.

9. A herbicidal composition which comprises a herbicidally effective amount of the compound according to claim 1 as an active ingredient and an inert carrier.

10. A herbicidal composition comprising a herbicidally effective amount of the compound according to claim 2 as an active ingredient and an inert carrier.

11. A herbicidal composition comprising a herbicidally effective amount of the compound according to claim 3 as an active ingredient and an inert carrier.

12. A herbicidal composition comprising a herbicidally effective amount of the compound according to claim 4 as an active ingredient and an inert carrier.

13. A herbicidal composition comprising a herbicidally effective amount of the compound according to claim 5 as an active ingredient and an inert carrier.

14. A herbicidal composition comprising a herbicidally effective amount of the compound according to claim 6 as an active ingredient and an inert carrier.

15. A herbicidal composition comprising a herbicidally effective amount of the compound according to claim 7 as an active ingredient and an inert carrier.

16. A herbicidal composition comprising a herbicidally effective amount of the compound according to claim 8 as an active ingredient and an inert carrier.

17. A method for controlling weeds which comprises applying a herbicidally effective amount of the compound according to claim 1 to the area where the weeds grow or will grow.

18. A compound of the formula:

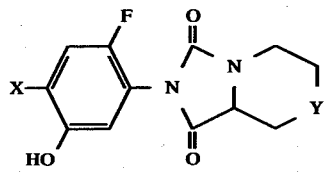

wherein X is a chlorine atom or a bromine atom and Y is —CH$_2$—, —S— or —SO$_2$—.

* * * * *

UNITED STATES PATENT AND TRADEMARK OFFICE
CERTIFICATE OF CORRECTION

PATENT NO. : 4,437,877
DATED : March 20, 1984
INVENTOR(S) : Eiki NAGANO et al

It is certified that error appears in the above-identified patent and that said Letters Patent is hereby corrected as shown below:

In the Heading of the Patent, in the category

"Foreign Application Priority Data", delete

"Dec. 4, 1981  [JP]   Japan.................56-19036" and insert --Dec. 4, 1981  [JP]   Japan...........56-196036--.

Signed and Sealed this

Nineteenth Day of June 1984

[SEAL]

Attest:

GERALD J. MOSSINGHOFF

Attesting Officer

Commissioner of Patents and Trademarks